United States Patent [19]

Tan et al.

[11] Patent Number: 5,336,837

[45] Date of Patent: Aug. 9, 1994

[54] SEPARATION OF DIETHYLBENZENE ISOMERS ON SILICALITE IN THE PRESENCE OF HIGH PRESSURE CARBON DIOXIDE AND PROPANE

[75] Inventors: Chung-Sung Tan, Hsinchu; Shiaw-Tseh Chiang, Taoyuan, both of Taiwan

[73] Assignee: Taiwan Styrene Monomer Corporation, Taipei, Taiwan

[21] Appl. No.: 37,995

[22] Filed: Mar. 25, 1993

[51] Int. Cl.$^5$ .................................................. C07C 7/12
[52] U.S. Cl. .................................... 585/828; 585/831
[58] Field of Search .............................. 585/828, 831

[56] References Cited

U.S. PATENT DOCUMENTS 5,227,570  7/1993  Tan ........................................ 585/822

OTHER PUBLICATIONS deRosset et al., Separation Science and Technology, 15(3), 637–653, 1980.
Lu et al., Ind. Eng. Chem. Res., vol. 26, No. 10, 2024–2028, 1987.
Flanigen et al., Nature, vol. 271, 512–516, 1978.

*Primary Examiner*—Anthony McFarlane
*Assistant Examiner*—Nhat D. Phan
*Attorney, Agent, or Firm*—Konneker Bush Hitt & Chwang

[57] ABSTRACT

A process for separating p-diethylbenzene from a diethylbenzene isomers mixture by selective adsorption of p-diethylbenzene on a silicalite adsorbent is disclosed in the present invention, wherein a compressed high pressure $CO_2$ or propane is used as a carrier for carrying a fixed amount of the diethylbenzene isomers mixture to the silicalite adsorbent bed for the selective adsorption, a first stage effluent stream containing a rich meta-diethylbenzene (m-DEB) and/or ortho-diethylbenzene (o-DEB), but having substantially no para-diethylbenzene (p-DEB) is eluted from the adsorbent bed; when p-DEB of the mixture starts to appear in the first stage effluent stream, a much higher pressurized $CO_2$ or propane used as a desorbent is then fed into the adsorbent bed, and a second stage effluent stream conaining a rich p-DEB, but having substantially no other DEB isomers is thereby eluted from the adsorbent bed. The diethylbenzene isomers procucts contained in the first and second effluent streams, respectively, can be easily separated from $CO_2$ or propane simply by reducing the pressure thereof, wherein the resulting $CO_2$ or propane can be re-compressed and recycled.

20 Claims, 6 Drawing Sheets

SEPARATION OF DIETHYLBENZENE ISOMERS ON SILICALITE IN THE PRESENCE OF HIGH PRESSURE CARBON DIOXIDE AND PROPANE

FIELD OF THE INVENTION

The present invention is directed to the adsorptive separation of p-diethylbenzene from a p-diethylbenzene isomers mixture, wherein silicalite is used as an adsorbent and carbon dioxide or propane is used as a carrier or desorbent depending on its pressure.

BACKGROUND OF THE INVENTION p-Diethylbenzene (p-DEB) is used as the desorbent in the Parex process (Derosset, et al., Sep. Sci. Technol. 15, 637 (1980)) for the separation of p-Xylene for xylene isomers and as the cross-linking agent in the synthesis of polymeric resins. One of the ways to produce p-DEB is to separate mixed DEB supplied from ethylbenzene alkylation process (Wang, et al., U.S. Pat. No. 4,950,835). Because of the very close boiling points possessed by DEB isomers: for example, ortho-diethylbenzene (o-DEB) is 183° C.; meta-diethylbenzene (m-DEB) is 180°–181° C.; and para-diethylbenzene (p-DEB) is 184° C., it is difficult to have a complete separation by distillation. The cryogenic separation is an alternative, however, it is in general costly.

At present, while several adsorption processes have been developed for separation of diethylbenzene isomers, the selective adsorption process using zeolite as a adsorbent in liquid phase is most commonly used and it is recognized as a most economic one. For example, disclosed in the U.S. Pat. No. 4,051,192 (1977), Neuzil, et al. used about 70 $cm^3$ of the zeolite X ion-exchanged with barium (Ba) and potassium (K) to recover 90.7% of p-DEB at the temperature 450 K. and the pressure 136 atm, wherein toulene was used as the desorbent; Lu and. Lee, in their article, Ind. Eng. Chem., Res. 26, 2024 (1987), tested several adsorbents and desorbents for separation p-DEB from mixed DEB and found that the CDZ zeolite was the most appropriate one to obtain p-DEB with a purity over 95% in the temperature range from 393–463 K. and in the pressure range from 1.5 to 3.0 atm. wherein o-xylene was used as the desorbent.

Santacesaria, et al. in their article, entitled "Separation of Xylenes on Y Zeolites in the Vapor Phase. 1. Determination of the Adsorption Equilibrium Parameters and of the Kinetic Regime", Ind. Eng. Chem. Processes Des. Dev. 24, 78–83 (1985) reported the separation of xylene isomers under gas phase operation was found to be superior to that under liquid phase operation. The improvement was attributed to higher mass transfer rate in vapor. But for both operations a desorbent is required. Some of $C_8$ aromatics were the most commonly employed desorbent.

Several methods of separation using desorbent as mentioned above require using aromatic compounds as a desorbent, therefore, a distillation operation is thereby needed in order to separate desorbent from product, which is energy intensive and increased separation cost.

TAN, Chung-Sung, one of the inventors of the present invention, and Tsay, Jeng-Leei, in their article, entitled "Separation of Xylene Isomers on Silicalite in Supercritical and Gaseous Carbon Dioxide" Ind. Eng. Chem. Res., Vol. 29, 502–504 (1990) reported an experimental study of the separation of an equal amount of p- and m-xylenes on silicalite using carbon dioxide as the carrier and the desorbent. The results showed that the operations in the gaseous phase carbon dioxide offered a better separation efficiency over those at supercritical conditions. The effects of temperature, pressure and flow rate on the effectiveness of separation were also examined. It was found that, for a pulse of 1.0 $cm^3$ of xylene isomers and 39.5 g of silicalite, the most appropriate operating conditions were a temperature of around 358 K., a pressure of 476 atm and a flow rate of about 15.0 $cm^3$/min.

TAN, Chun-Sung, in his U.S. Pat. application Ser. No. 07/801,531 filed on Dec. 2, 1991 (which was allowed on Dec. 24, 1992), disclosed a process for separating ethylbenzene and p-xylene from xylene isomers mixture, wherein a compressed high pressure vapor phase $CO_2$ was used as the carrier. A fixed amount of xylene isomers was fed into a silicalite adsorbent bed for adsorption operation, and a first stage effluent stream containing a rich m-xylene and/or o-xylene, but having substantially no ethylbenzene and p-xylene was obtained from the adsorbent bed, wherein when ethylbenzene or p-xylene contained in the mixture started to appear in the first stage effluent stream, a supercritical $CO_2$ used as a desorbent was introduced into the adsorbent bed and a second stage effluent stream containing a rich ethylbenzene and p-xylene, but having substantially no other xylene isomers is thereby obtained. Preferably, the first and the second effluent streams could be separately sent into different activated carbon adsorbent beds to adsorb isothermally and isobarically the said xylene isomers products, and the resulting substantially pure $CO_2$ exiting from said activated carbon adsorbent bed could be recovered and repeatedly used. Alternatively, the introduction of said high pressure gaseous $CO_2$ could continue until m-xylene, o-xylene and p-xylene were completely separated from the mixture, and then a supercritical $CO_2$ was introduced as a desorbent such that a second stage effluent stream containing a rich ethylbenzene (EB) was obtained.

The object of the present invention is to provide a process for separation of diethylbenzene isomers on silicalite in high pressure gaseous $CO_2$ or propane to produce a high purity of p-diethylbenzene.

Another object of the present invention is to provide a process for separation of diethylbenzene isomers on silicalite in high pressure gaseous $CO_2$ or propane to to produce a high purity of p-diethylbenzene with a high productivity, that is, the amount of the adsorbent used is relatively lower.

The other object of the present invention is to provide a process for separation of diethylbenzene isomers on silicalite in a high pressure gaseous $CO_2$ or propane to produce a high purity of p-diethylbenzene, wherein $CO_2$ or propane is used as a carrier in the first stage of the process and as a desorbent in the second stage of the process, and by reducing the pressure of the effluent stream from the adsorbent bed the diethylbenzene isomers products could be separated from the carrier or desorbent.

SUMMARY OF THE INVENTION

A process for separating p-diethylbenzene from a diethylbenzene isomers mixture comprises: introducing a fixed amount of diethylbenzene isomers mixture into a silicalite adsorbent bed for selective adsorption by using a high pressure gaseous $CO_2$ or propane as a carrier such that a first stage effluent stream containing a rich meta-diethylbenzene (m-DEB) and/or ortho-diethylbenzene (o-DEB), but having substantially no para-diethylbenzene (p-DEB) is eluted from the adsorbent bed; introducing a much higher pressurized $CO_2$ or propane as a desorbent into the adsorbent bed, when p-DEB of the mixture starts to appear in the first stage effluent stream, such that a second stage effluent stream conaining a rich p-DEB, but having substantially no other DEB isomers is eluted from the adsorbent bed. DEB isomers contained in the first and second streams, respectively, could be easily separated from $CO_2$ or propane and recovered simply by reducing the pressure thereof, wherein the resulting $CO_2$ or propane could be re-compressed and recycled.

In the present process, when almost all of the non-para-diethylbenzene isomers are eluted from the adsorbent bed, the adsorbed p-diethylbenzene isomers could be thereby desorbed by introducing a much higher pressurized $CO_2$ or propane into the adsorbent bed, preferably a supercritical $CO_2$ or propane. As a result, the use of commonly employed aromatics desorbent can be avoided and in consequence, the distillation operation usually required for separation of diethylbenzene isomers products from the aromatics desorbent could also be eliminated.

DETAILED DESCRIPTION OF THE INVENTION

Figure 1:
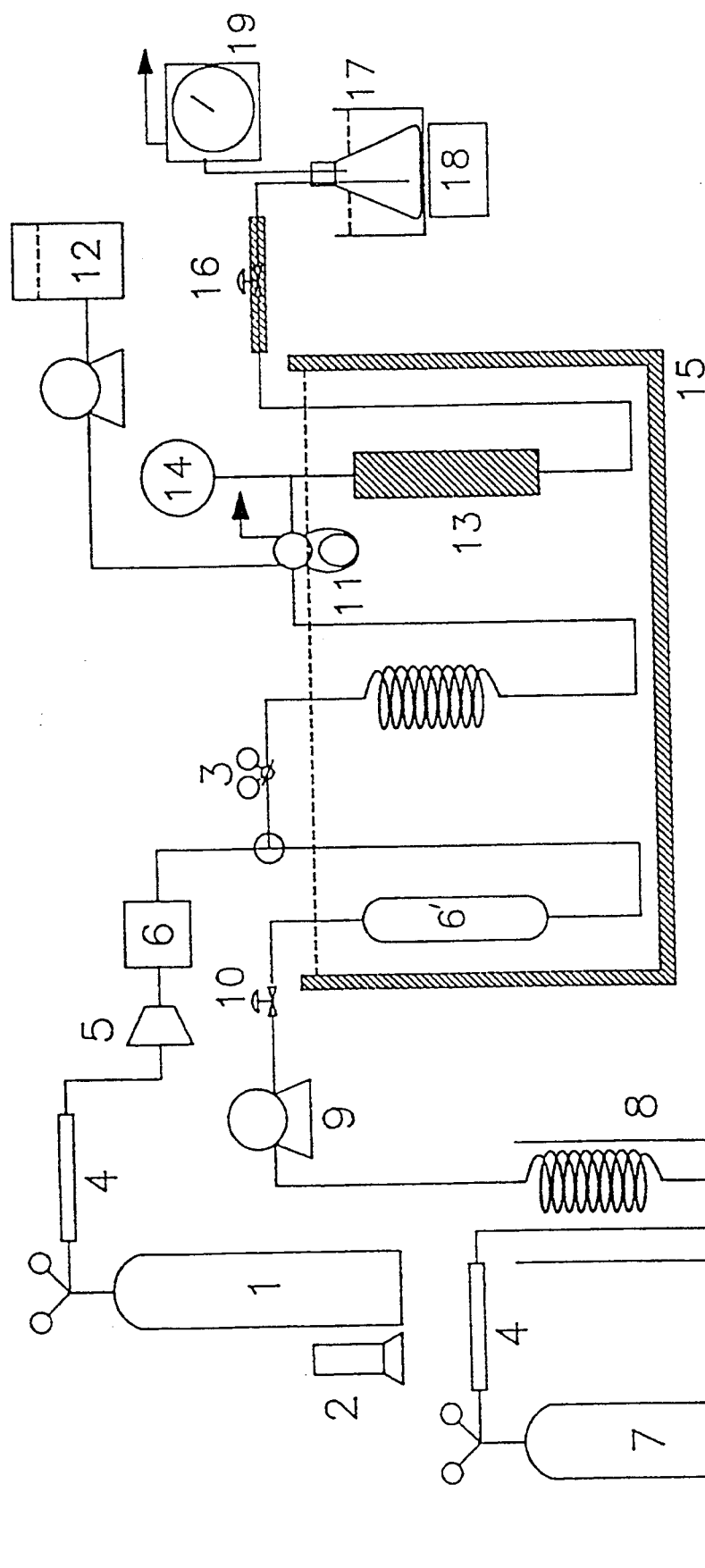
FIG. 1 is a schematic diagram of a process for adsorptive recovery of p-diethylbenzene from a diethylbenzene isomers mixture, wherein 1 is a $CO_2$ cylinder, 2 is a heater, 3 is a regulator, 4 is zeolite 4A, 5 is a compressor, 6, 6' is a surge tank, 7 is a propane cylinder, 8 is a cooler, 9 is a minipump, 10 is a needle valve, 11 is sampling valve, 12 is DEB isomers feed, 13 is adsorbent packing bed, 14 is a pressure gauge, 15 is an oil bath, 16 is an expansion valve, 17 is a cold trap, 18 is a magnetic stirrer, and 19 is a wet test meter.

Because of more stringent specification required on purity of p-DEB in the Parex process, the industry is interested in having a new process providing a more economic separation process for producing a desired purity of p-DEB is therefore needed.

The present inventors present an efficient process for separating a diethylbenzene (DEB) isomers mixture to produce a substantially 100% pure p-diethylbenzene (p-DEB). In particular, when DEB isomers other than p-DEB are first eluted from the adsorbent bed, the present process uses a much higher pressurized $CO_2$ or propane, preferably a supercritical state $CO_2$ or propane, to desorb the absorbed p-DEB isomers, and the conventional $C_8$ aromatics are not used for desorption. As a result, the present process, in addition to its high recovery and productivity, can prevent the disadvantage of high energy consumption and capital cost by distillation process which is commonly employed for separating the aromatics desorbent from the DEB isomers products.

The present invention offers a process for separating p-DEB from DEB isomers mixture, additionally containing m-xylene and/or o-xylene, which comprises:

a) separating p-diethylbenzene from the mixture by selective adsorption of the p-diethylbenzene on a silicalite adsorbent bed, wherein a fixed amount of the mixture is introduced into the adsorbent bed by using a compressed high pressure gaseous $CO_2$ stream as a carrier, and a first stage effluent stream containing a diethylbenzene isomers composition having substantially no p-diethylbenzene is obtained from the adsorbent bed;

b) desorbing the adsorbed p-diethylbenzene from the adsorbent bed when the diethylbenzene isomers composition contained in the first stage effluent stream has a desired p-diethylbenzene percentage, wherein a much higher pressurized $CO_2$ stream, as a desorbent, is fed to the adsorbent bed to obtain a second stage effluent stream containing a diethylbenzene isomers composition having substantially pure p-diethylbenzene; and c) reducing the pressure of the second stage effluent stream such that the $CO_2$ is removed from the second stage effluent stream by evaporization, whereby a substantially pure p-diethylbenzene in liquid phase and a substantially pure gaseous $CO_2$ are obtained.

The above-mentioned process can be further proceeded with an additional step before, during or after step c) as follows:

d) reducing the pressure of the first stage effluent stream such that the $CO_2$ is removed from the first stage effluent stream by evaporization, whereby m-diethylbenzene and o-diethylbenzene in liquid phase and a substantially pure gaseous $CO_2$ are obtained.

Preferably, the resulting gaseous $CO_2$ from step c) and step d) are re-compressed and recycled to step a) and step b), respectively.

DEB isomers mixture suitable to be used in the present process contains at least two kinds of DEB isomers, and one of them is p-DEB isomer. Preferably, the DEB isomers mixture is the DEB isomer mixture which can be obtained in large quantity in the petrochemical industry. For example, a DEB isomers mixture having a weight ratio of m-DEB to p-DEB of about 2:1 was obtained after distillation following the ethylbenzene alkylation reaction in the production plant of the Taiwan Styrene Monomer Co.. In consequence, in one of the preferred embodiments of present invention a mixture of 66.7 wt % m-DEB and 33.3 wt % p-DEB is used as a mixture feed. Nevertheless, a mixture containing o-, m- and p-DEB isomers can also be applied in the present process. Because o-xylene and m-xylene can be simultaneously separated from the adsorbed p-xylene in a silicalite adsorbent bed as instructed in our prior U.S. Pat. application Ser. No. 07/801,531 filed on Dec. 2, 1991 (which was allowed on Dec. 4, 1992), it is believed that m-DEB and o-DEB will be eluted from the silicalite adsorbent bed and p-DEB will be selectively adsorbed on the silicalite adsorbent bed in the step a). The disclosure of U.S. Pat. application Ser. No. 07/801,531 is incorporated herein as a reference. In addition, the inventors had also used the present process to separate a mixture containing 96 wt % p-DEB and 4 wt % o-DEB, and a pure p-DEB can thereby be obtained.

In an experimental study, the present inventors have tried to use different kinds of adsorbents, such as zeolite X, zeolite Y and activated carbon in addition to silicalite, and the results showed that silicalite has a satisfactory adsorptive performance.

Silicalite is a polymorgh of silica whose structure is similar to that of ZSM-5. It is formed and inter linked by a 5.1 Å×5.5 Å elliptic straight-line pore and a 5.4 Å×5.6 Å approximate circular zig-zag pore. The cross-section of these pores is formed by oxygen rings consisting of 10 oxygen atoms. Only the particle with a diameter of less than 6 Å A can pass through the pores. (Flanigen, et al. Nature, 271, 512–516, 1978). The major difference between silicalite and ZSM-5 is that the crystal of silicalite is aluminum free. In the following examples of the present invention, a silicalite pellet in cylinder form containing 20% $Al_2O_3$ binder which is available from commerce is used as a starting material.

As instructed in U.S. patent application Ser. No. 07/801,531, the present inventors believe that silicalite in a higher Si/Al ratio has a better separation performance and it is further believed that the performance of powder-form silicalite having a mesh No. 24–32 is better than the cylinder-form silicalite pellets having a dimension of 1.55 mm (D)×6.2 mm (L).

The compressed high pressure gaseous $CO_2$ stream in step a) has a temperature ranging from 323 K. to 393 K., preferably, 353–373 K.; a pressure ranging from 27 atm to 48 atm, preferably 30–40 atm; and is introduced into the adsorbent bed at a flow rate of 15.0–40.0 cm$^3$/min, preferably 25–35 cm$^3$/min, at the above-described $CO_2$ temperature and pressure.

The much higher pressurized $CO_2$ used in step b) has a pressure higher than that of said compressed high pressure gaseous $CO_2$ stream used in step a), preferably a supercritical $CO_2$ fluid. (The critical pressure of $CO_2$ is 71.8 atm.) In principle, the higher the pressure, the quicker the desorptive process; however, when pressure is increased, the equipment and operating costs are also increased. As a result, a pressure between 50–102 atm is most commonly used.

In the above step c), basically, the pressure must be sufficiently reduced in order to evaporate $CO_2$ from the second stage effluent stream, i.e. to generate a gas-liquid phase separation. Likewise, in the above step d) the pressure must be sufficiently reduced in order to evaporate $CO_2$ from the first stage effluent stream.

In addition to $CO_2$ being used as a carrier, the present inventors also found that propane can be used as a carrier for adsorptive separation of a DEB isomers mixture on silicalite. Although silicalite processes adsorptive property to some extent to organic substance, the present inventors observed that propane could be used as a carrier or a desorbent with no influence to the effectiveness of adsorptive separation of a DEB isomers mixture on silicalite.

Using propane as a carrier in the present invention, a process for separating a DEB isomers mixture comprises:

a') separating p-diethylbenzene from the mixture by selective adsorption of the p-diethylbenzene on a silicalite adsorbent bed, wherein a fixed amount of the mixture is introduced into the adsorbent bed by using a compressed high pressure gaseous propane stream as a carrier, and a first stage effluent stream containing a diethylbenzene isomers composition having substantially no p-diethylbenzene is obtained from the adsorbent bed;

b') desorbing the adsorbed p-diethylbenzene from the adsorbent bed when the diethylbenzene isomers composition contained in the first stage effluent stream has a desired p-diethylbenzene percentage, wherein a much higher pressurized propane stream, as a desorbent, is fed to the adsorbent bed to obtain a second stage effluent stream containing a diethylbenzene isomers composition having substantially pure p-diethylbenzene; and c') reducing the pressure of the second stage effluent stream such that the propane is removed from the second stage effluent stream by evaporation, whereby a substantially pure p-diethylbenzene in liquid phase and a substantially pure gaseous propane are obtained.

The above-mentioned process can be further proceeded with an additional step before, during or after step c') as follows:

d') reducing the pressure of the first stage effluent stream such that the propane is removed from the first stage effluent stream by evaporation, whereby m-diethylbenzene and o-diethylbenzene in liquid phase and a substantially pure gaseous propane are obtained.

Preferably, the resulting gaseous propane from step c') and step d') are re-compressed and recycled to step a') and step b'), respectively.

Step a') as stated above, a compressed high pressure vapor phase propane is used in the selective adsorptive separation operation as a carrier, wherein the operating temperature range is from 383 K. to 473 K., preferably, 403–453 K.; the pressure range is from 3 atm to 13 atm, preferably 5–10 atm; the flow rate of propane is between 9.0–40.0 cm$^3$/min, preferably 13–18 cm$^3$/min, at the operating temperature and pressure.

The much higher pressurized propane for desorptive operation in step b') has a pressure much higher than that of said compressed high pressure gaseous propane stream used in step a'), preferably a supercritical propane fluid. (The critical pressure of propane is 42 atm). In principle, the higher the pressure, the quicker the desorptive process; however, when the pressure is increased, the equipment and operating cost are also increased. As a result, a pressure between 27–70 atm is most commonly used.

In the above step c'), basically, the pressure muse be sufficiently reduced in order to evaporate propane from the second stage effluent stream, i.e. to generate a gas-liquid phase separation. Likewise, in the above step d'), the pressure must be sufficiently reduced in order to evaporate propane from the first stage effluent stream.

The following examples are only used to illustrate the present invention and not meant to be limiting.

EXAMPLE 1

Separation of a mixture of p-diethylbenzene (p-DEB) and m-diethylbenzene (m-DEB)

The present example uses the separation system illustrated in FIG. 1 to separate a mixture with a composition of 66.7 wt % m-DEB and 33.3 wt % p-DEB.

Silicalite pellets having a pore opening of about 6A, a Si/Al ratio of 1040, and a dimension of 1.55 mm (D)×6.2 mm (L) available from Union Carbide Corp. were used as adsorbent. The physical properties of silicalite used are listed in the following Table 1.

TABLE 1

| | |
|---|---|
| Surface area (BET) = | 343.1 m$^2$/g (<600Å) |
| Pore volume (N$_2$) = | 0.2553 cm$^3$/g (<600Å) |
| Pore volume (Hg) = | 0.3272 cm$^3$/g (<37.5Å–325 μm) |
| Bulk density = | 0.7532 g/cm$^3$ |
| Particle density = | 1.2025 g/cm$^3$ |
| Ture density = | 1.9825 g/cm$^3$ |
| Bed voidage = | 0.3736 |
| Particle porosity = | 0.3934 |

Surface area as shown in Table 1 is measured by Brunauer-Emmett-Teller (BET) method, and pore volume is measured by nitrogen adsorption and mercury method. The data show that bigger pores (>600 Å) have a certain percentage.

Before use, silicalite pellets were crushed to smaller particles and sized by mesh No. 24 and mesh No. 32 sieves. The particles so sized were dried at 120° C. in an oven for four hours in order to remove water contained therein, and then activated at 600° C. for 24 hours. The silicalite particles were weighed as soon as the temperature dropped to 120° C. and packed into the packing bed 13.

Packing bed 13 is a stainless steel 316 column of 2.12 cm i.d. and 25 cm in length. About 40.0 g of the silicalite particles were packed into said packing bed 13. In order to achieve an uniform flow distribution in the packing bed 13, glass beads of 0.07 cm diameter were packed above and below the silicalite packing to heights of 5.0 cm, respectively.

A mixture prepared by mixing a weight ratio of research-grade m-DEB : p-DEB as 2:1 was used as a mixture feed. The mixture of m-DEB and p-DEB was fed to a six-port sampling valve 7 (model No. 7010, Rheodyne Inc.) by a minipump 9. The volume of the sampling loop was 1.0 cm$^3$. Carbon dioxide with a purity of at least 99.7% located in cylinder 1 was first passed through a zeolite 4A bed 4 to remove any water vapor and hydrocarbons, and it was recompressed by a diaphram compressor 5 (Superpressure Inc.) and sent to a surge tank 6. In each experiment, the pressure was maintained within ±0.34 atm (5 psi) of the desired value. The temperature was controlled in an oil bath 15 whose accuracy was about 0.5° C. A preheating coil was immersed in the bath to allow the temperature to reach the desired temperature.

Before injection of the mixture, the six-port sampling valve 7 was switched to let carbon dioxide bypass the sampling loop. Expansion valve 16 was adjusted to let carbon dioxide fluid reach a stable value and sampling valve 7 was then switched to allow the carbon dioxide carrying the mixture to flow into the packing bed 13. The effluent fluid from the packing bed 13 passed through expansion valve 16 and flowed into a cold trap 17 whose temperature was about −10° C., p-DEB and m-DEB were collected in the cold trap 17 which contained 0.5 cm$^3$ alcohol with a purity of 95% and 0.5 g of cumene used as an internal standard. Samples of 2.0 μL collected in the cold trap 17 were sent to a GC (model 8700 F, China Chromatography) at an interval of 20 min. for composition analysis. The flow rate of packing bed 13 was determined by measuring the volume of the gas with a wet test meter 19. Due to carbon dioxide being soluble in alcohol contained in the cold trap, carbon dioxide has to be fed into the alcohol for saturation for two hours before adjusting the flow rate. Furthermore, as CO$_2$ flow rate of the present example is indicated by a flow rate within the system and the CO$_2$ flow rate is measured by a wet test meter at room conditions, conversions were made by using the CO$_2$ densities within the system and in the laboratory.

The total amount of p-DEB and m-DEB collected in the cold trap 17 were determined by measuring the final concentrations in the cold trap. These amounts were compared with those calculated by integrating the response curves. The agreements were satisfactory. The amounts collected were also found to be close to the amounts injected (deviation less than 5%). The results of experiments conducted under various combinations of temperature, pressure and flow rate are shown in the following Table 2, and some of typical testing results are also presented in FIG. 2.

TABLE 2

| T (K) | P (atm) | Q (cm$^3$/min) | $t_m$[a] (min) | $RC_m$[b] (%) | $RC_p$[c] (%) |
|---|---|---|---|---|---|
| Pressure Effect | | | | | |
| 363 | 27.2 | 14.8 | 368.6 | 100.0 | 100.0 |
| 363 | 34.0 | 15.0 | 272.7 | 100.0 | 100.0 |
| 363 | 40.8 | 15.0 | 234.4 | 99.7 | 94.3 |
| 363 | 47.6 | 14.9 | 184.5 | 96.5 | 87.3 |
| 363 | 61.2 | 15.0 | 111.4 | 76.6 | 34.1 |
| 363 | 74.8 | 14.9 | 81.2 | 54.1 | 17.1 |
| Temperature Effect | | | | | |
| 353 | 34.0 | 15.0 | 385.6 | 100.0 | 100.0 |
| 363 | 34.0 | 15.0 | 272.7 | 100.0 | 100.0 |
| 373 | 34.0 | 15.1 | 251.7 | 100.0 | 100.0 |
| 383 | 34.0 | 15.1 | 191.1 | 97.5 | 84.5 |
| 393 | 34.0 | 15.1 | 127.5 | 96.9 | 81.2 |
| Flow Rate Effect | | | | | |
| 353 | 34.0 | 15.0 | 385.6 | 100.0 | 100.0 |
| 353 | 34.0 | 20.2 | 289.8 | 100.0 | 100.0 |
| 353 | 34.0 | 30.1 | 235.1 | 100.0 | 100.0 |
| 353 | 34.0 | 40.1 | 147.6 | 99.1 | 95.1 |
| 363 | 34.0 | 15.0 | 272.7 | 100.0 | 100.0 |
| 363 | 34.0 | 19.9 | 217.6 | 100.0 | 100.0 |
| 363 | 34.0 | 29.9 | 149.7 | 100.0 | 100.0 |
| 363 | 34.0 | 34.7 | 126.4 | 98.5 | 91.4 |
| 363 | 34.0 | 40.0 | 110.4 | 95.3 | 84.8 |
| 373 | 34.0 | 15.1 | 251.7 | 100.0 | 100.0 |
| 373 | 34.0 | 19.8 | 167.2 | 100.0 | 100.0 |
| 373 | 34.0 | 25.2 | 136.6 | 97.6 | 88.9 |
| 373 | 34.0 | 40.2 | 82.4 | 95.4 | 83.6 |

[a] The mean retention time $\bar{t}_m$ in Table 2 is defined as $$\bar{t}_m = \int_0^{t_0} C^* t\, dt / \int_0^{t_0} C\, dt$$

wherein C is the concentration of m-DEB, t is time, and to is the total time for complete separation of m-DEB.
[b] $RC_m$ is the recovery of m-DEB, which is defined as the amount of m-DEB collected from the packing bed with a purity higher than 99% over the total experimental period divided by the amount injected.
[c] $RC_p$ is the recovery of p-DEB, which is defined as the amount of p-DEB collected from the packing bed with a purity higher than 99% over the total experimental period divided by the amount injected.

Considering both the recovery and operating time, it is found out from Table 2 that a pressure of about 34 atm, a temperature of about 363 K. and a flow rate of 30 cm$^3$/min are the most appropriate operating conditions.

Figure 2:
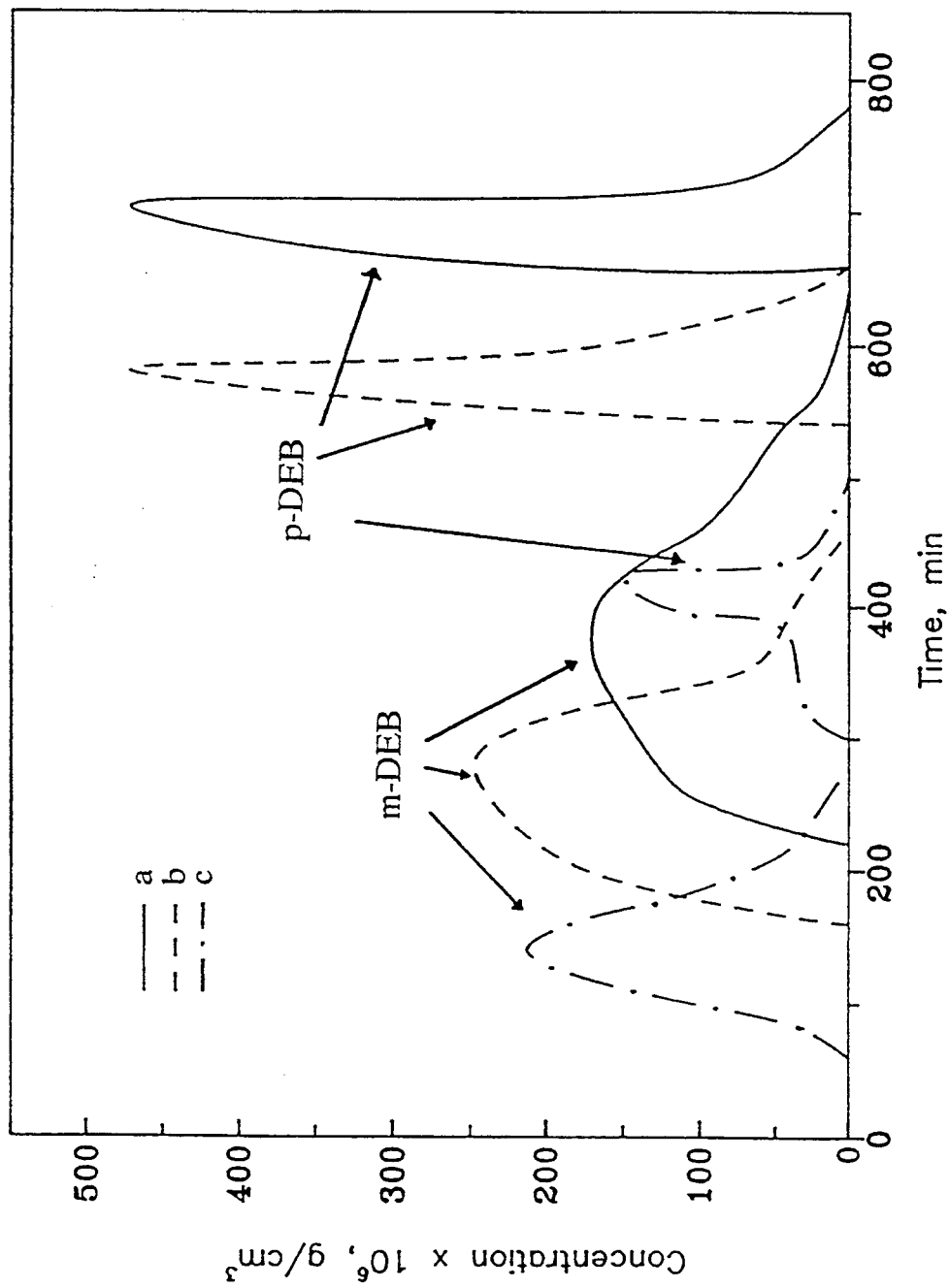
FIG. 2 is plot showing p-DEB and m-DEB response curves in an adsorptive separation under different pressure, temperature and $CO_2$ flow rate, wherein curve a) represents temperature 353 K., $CO_2$ flow rate: 15 $cm^3$/min; and the pressure is 34 atm when the time is less than 600 min; the pressure is 102 atm when the time is greater than 600 min; curve b) represents temperature: 363 K.; $CO_2$ flow rate: 15 $cm^3$/min, and the pressure is 34 atm when the time is less than 540 min; the pressure is 102 atm when the time is greater than 540 min; and curve c) represents 363 K.; $CO_2$ flow rate is 30 $cm^3$/min; and the pressure is 34 atm when the time is less than 380 min; and the pressure is 102 atm when the time is time is greater than 380 min.
Figure 3:
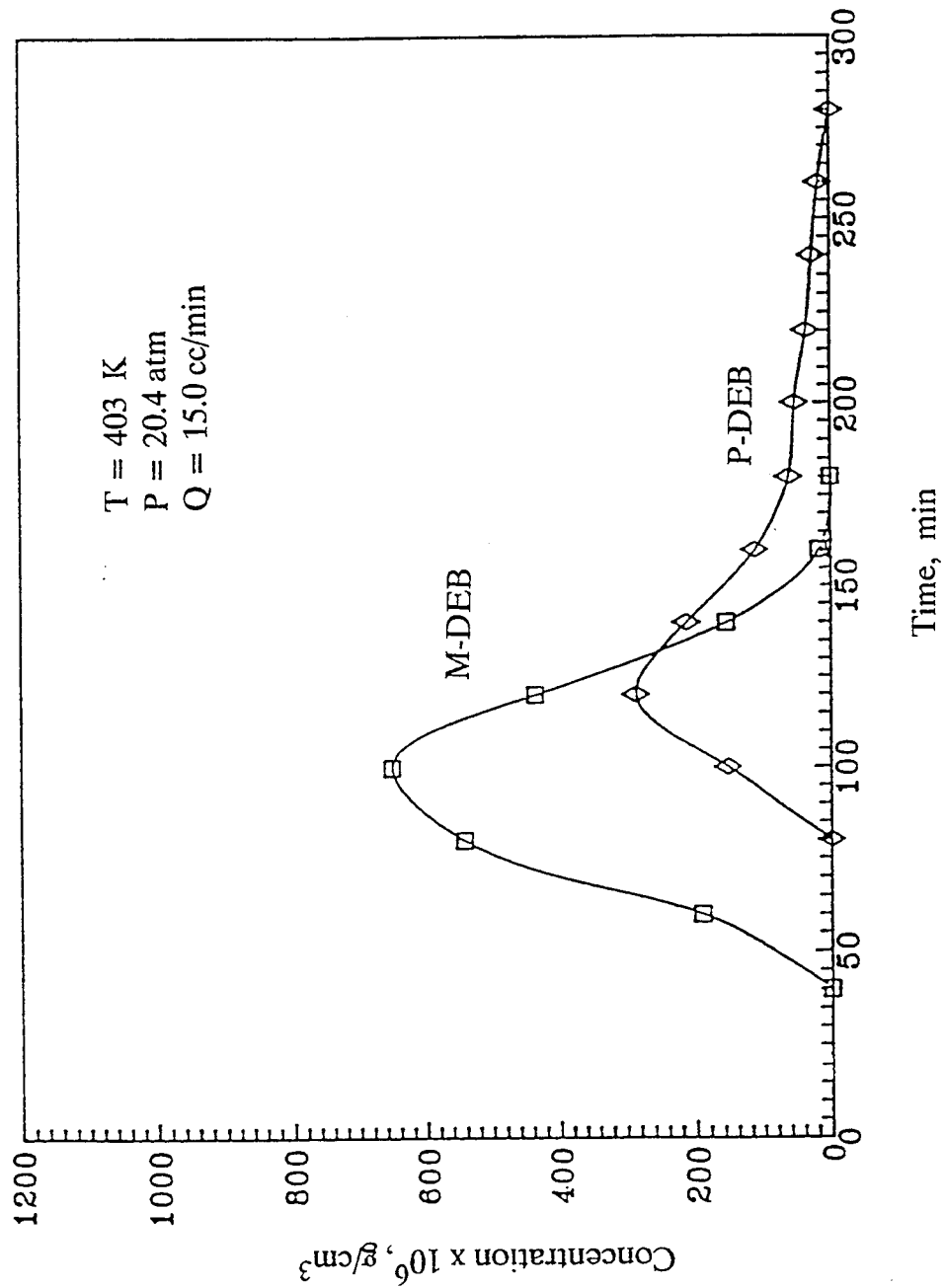
FIG. 3 is a plot showing the response curve of p-DEB and m-DEB under 20.4 atm, 403 K. and propane flow rate of 15.0 cc/min.

In order to further reduce the separation cycle time, it is suggested that the operating pressure is to be suddenly increased to 102 atm as soon as most of m-DEB component is recovered from the effluent fluid in order to increase p-DEB solubility in CO$_2$ so that the adsorbed p-DEB can be desorbed from the silicalite more quickly as shown in FIG. 2.

EXAMPLE 2

Separation of p-DEB and m-DEB

The procedures of Example 1 were repeated except that propane is used in place of $CO_2$ as a carrier for mixture feed, propane located within cylinder 7 must be first cooled with a cooler 8, and then sent to a surge tank 6' by a minipump 9 and other different combinations of operating conditions. The results are shown in Table 3, some of response curves in Table 3 are shown in FIG. 3 through FIG. 6.

Figure 4:
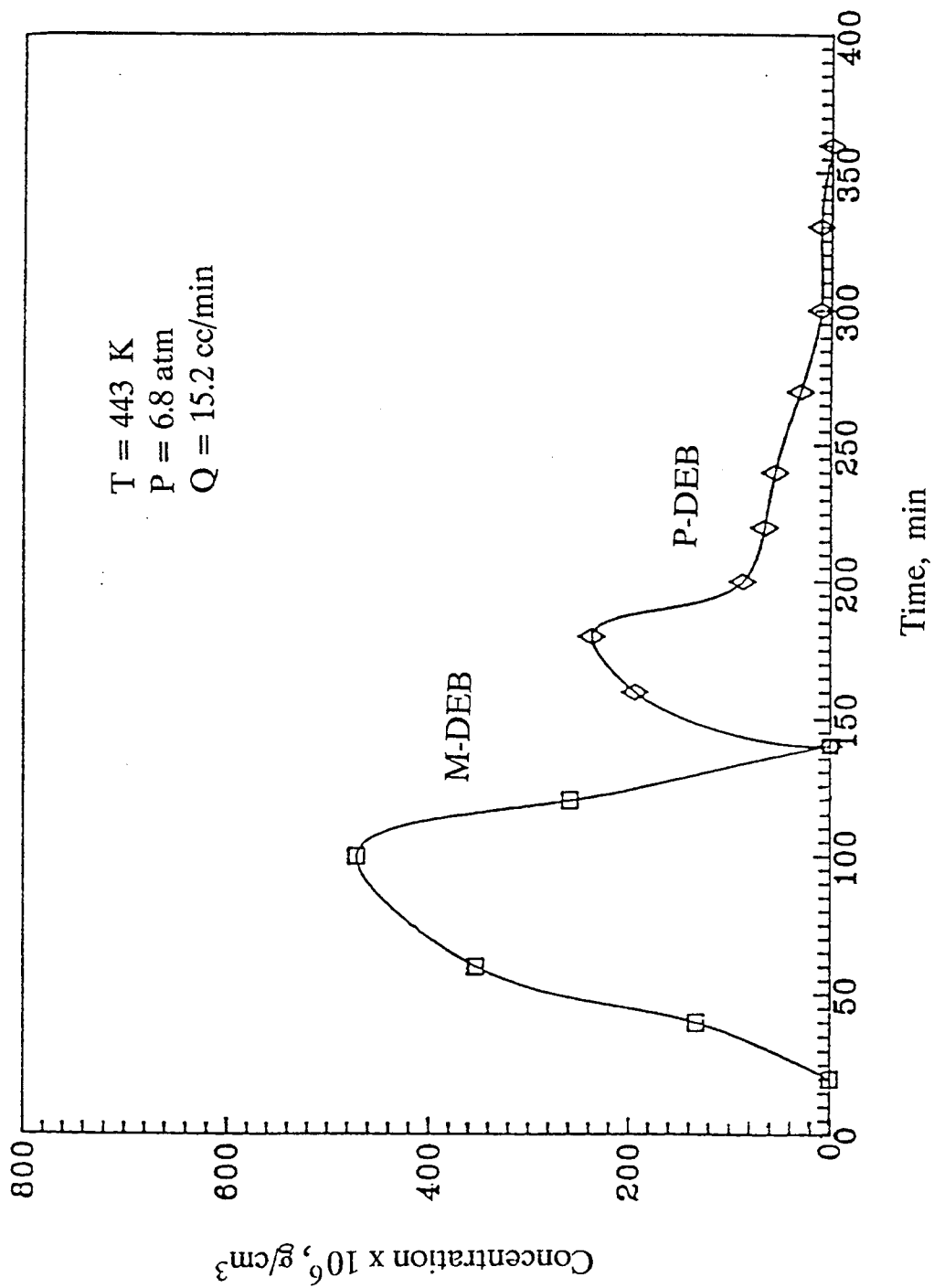
FIG. 4 is a plot showing the response curve of p-DEB and m-DEB under 6.8 atm, 443 K. and propane flow rate of 15.2 cc/min.

The data of Table 3 show that the operating conditions of 443 K., 6.8 atm and 15 cm³/min has a better separation. The recovery of both p-DEB and m-DEB under these operating conditions are 100%. Likewise, in order to further reduce the separation cycle time, it is suggested that the operating pressure may be suddenly increased to a pressure near critical point as soon as most of m-DEB component is eluted from the adsorbent bed in order to increase solubility of p-DEB in propane such that the adsorbed p-DEB can be desorbed from the silicalite more quickly. The data in FIG. 4 show that at the time of 150 min for separation operation, the pressure of propane may be increased to 55 atm.

TABLE 3

| T (K) | P (atm) | Q (cm³/min) | $t_m^{a)}$ (min) | $RC_m^{b)}$ (%) | $RC_p^{c)}$ (%) |
|---|---|---|---|---|---|
| Pressure Effect | | | | | |
| 363 | 13.6 | 15.0 | 430.1 | 50.9 | 34.3 |
| 363 | 20.4 | 14.9 | 262.8 | 26.4 | 7.9 |
| 363 | 27.2 | 14.9 | 141.9 | 15.7 | 6.8 |
| 403 | 6.8 | 15.3 | 174.2 | 100 | 100 |
| 403 | 13.6 | 15.0 | 130.0 | 88.7 | 66.9 |
| 403 | 20.4 | 15.1 | 98.8 | 54.3 | 23.8 |
| Temperature Effect | | | | | |
| 363 | 13.6 | 15.0 | 430.1 | 50.9 | 34.3 |
| 383 | 13.6 | 14.9 | 235.9 | 67.9 | 44.5 |
| 403 | 13.6 | 15.0 | 130.0 | 88.7 | 66.9 |
| 413 | 13.6 | 15.1 | 104.9 | 75.7 | 57.8 |
| 383 | 6.8 | 30.2 | 175.9 | 92.2 | 83.8 |
| 403 | 6.8 | 15.3 | 174.2 | 100 | 100 |
| 423 | 6.8 | 15.2 | 130.1 | 100 | 100 |
| 433 | 6.8 | 15.2 | 115.1 | 100 | 100 |
| 443 | 6.8 | 15.2 | 84.4 | 100 | 100 |
| 453 | 6.8 | 15.2 | 101.9 | 88.9 | 61.3 |
| 403 | 5.1 | 30.1 | 96.9 | 96.4 | 92.8 |
| 423 | 5.1 | 30.2 | 68.2 | 95.8 | 92.5 |
| Flow Rate Effect | | | | | |
| 443 | 6.8 | 15.2 | 84.4 | 100 | 100 |
| 443 | 6.8 | 24.9 | 76.0 | 94.7 | 79.5 |
| 443 | 6.8 | 40.1 | 65.6 | 88.2 | 59.2 |
| 403 | 13.6 | 20.0 | 98.5 | 85.2 | 54.0 |
| 403 | 13.6 | 15.0 | 130.0 | 88.7 | 66.9 |
| 403 | 13.6 | 9.8 | 196.5 | 90.2 | 67.2 |
| 413 | 13.6 | 15.1 | 104.9 | 75.7 | 57.8 |
| 413 | 13.6 | 10.1 | 148.2 | 80.1 | 58.5 |

The definitions of $a), b)$ and $c)$ are same as those shown in Table 2.

According to the information provided by the production plant of Taiwan Styrene Monomer Co., the DEB isomers mixture containing a similar composition used in this example from the distillation tower following the ethylbenzene alkylation action possesses a temperature of 473 K. and a pressure of 1.73 atm. As a result, considering both compression cost and the volume of the carrier used, it seems that the use of propane as a carrier in Example 2 is superior to the use of $CO_2$ in the separation operation of the DEB isomers mixture which is available from Taiwan Styrene Monomer Co.

What is claimed is:

1. A process for separating p-diethylbenzene from a diethylbenzene isomers mixture comprising:
   a) separating p-diethylbenzene from the mixture by selective adsorption of the p-diethylbenzene on a silicalite adsorbent bed, wherein a fixed amount of the mixture is introduced into the adsorbent bed by using a compressed high pressure gaseous $CO_2$ stream, having a pressure of 27–48 atm, as a carrier, and a first stage effluent stream containing a diethylbenzene isomers composition having substantially no p-diethylbenzene is obtained from the adsorbent bed; and
   b) desorbing the adsorbed p-diethylbenzene from the adsorbent bed when the diethylbenzene isomers composition contained in the first stage effluent stream has a desired p-diethylbenzene percentage, wherein a much higher pressurized $CO_2$ stream having a pressure of 50–102 atm, as a desorbent, is fed to the adsorbent bed to obtain a second stage effluent stream containing a diethylbenzene isomers composition having substantially pure p-diethylbenzene.

2. The process of claim 1 wherein the compressed high pressure gaseous $CO_2$ stream in step a) has a pressure of 30–40 atm.

3. The process of claim 1 wherein the much higher pressurized $CO_2$ stream in step b) is a supercritical $CO_2$ fluid.

4. The process of claim 1 wherein the second stage effluent stream in step b) contains a diethylbenzene isomers composition having a 98–100 wt % of p-diethylbenzene, 5. The process of claim 1 wherein the diethylbenzene isomers mixture contains m-diethylbenzene, o-diethylbenzene and p-diethylbenzene.

6. The process of claim 1 wherein the diethylbenzene isomers mixture has a composition of 33.3 wt % p-diethylbenzene and 66.7 wt % m-diethylbenzene.

7. The process of claim 1 wherein the selective adsorption in step a) is carried out under 323–393 K. and $CO_2$ flow rate of 15.–40.0 cm³/min 8. The process of claim 1 wherein following the step b) further comprises:
   c) reducing the pressure of the second stage effluent stream such that the $CO_2$ is removed from the second stage effluent stream by evaporation, whereby a substantially pure p-diethylbenzene in liquid phase and a substantially pure gaseous $CO_2$ are obtained.

9. The process of claim 8 wherein before, during or after the step c) further comprises:
   d) reducing the pressure of the first stage effluent stream such that the $CO_2$ is removed from the first stage effluent stream by evaporation, whereby m-diethylbenzene and o-diethylbenzene in liquid phase and a substantially pure gaseous $CO_2$ are obtained.

10. The process of claim 9 wherein the substantially pure gaseous $CO_2$ in step c) and step d) are re-compressed and recycled to the step a) or step b).

11. A process for separating p-diethylbenzene from a diethylbenzene isomers mixture comprising:
   a) separating p-diethylbenzene from the mixture by selective adsorption of the p-diethylbenzene on a silicalite adsorbent bed, wherein a fixed amount of the mixture is introduced into the adsorbent bed by using a compressed high pressure gaseous propane stream, having a pressure of 3–13 atm, as a carrier, and a first stage effluent stream containing a diethylbenzene isomers composition having substantially no p-diethylbenzene is obtained from the adsorbent bed; and b) desorbing the adsorbed p-diethylbenzene from the adsorbent bed when the diethylbenzene isomers composition contained in the first stage effluent stream has a desired p-diethylbenzene percentage, wherein a much higher pressurized propane stream having a pressure of 27–70 atm, as a desorbent, is fed to the adsorbent bed to obtain a second stage effluent stream containing a diethylbenzene isomers composition having substantially pure p-diethylbenzene.

12. The process of claim 11 wherein the compressed high pressure gaseous propane stream in step a) has a pressure of 5–10 atm.

13. The process of claim 11 wherein the much higher pressurized propane stream in step b) is a supercritical propane fluid.

14. The process of claim 11 wherein the second stage effluent stream in step b) contains a diethylbenzene isomers composition having 98–100 wt % of p-diethylbenzene.

15. The process of claim 11 wherein the diethylbenzene isomers mixture contains m-diethylbenzene, o-diethylbenzene and p-diethylbenzene.

16. The process of claim 11 wherein the diethylbenzene isomers mixture has a composition of 33.3 wt % p-diethylbenzene and 66.7 wt % m-diethylbenzene.

17. The process of claim 11 wherein the selective adsorption in step a) is carried out under 383–473 K. and propane flow rate of 9.0–40.0 $cm^3$/min.

18. The process of claim 11 wherein following the step b) further comprises:

c) reducing the pressure of the second stage effluent stream such that the propane is removed from the second stage effluent stream by evaporization, whereby a substantially pure p-diethylbenzene in liquid phase and a substantially pure gaseous propane are obtained.

19. The process of claim 18 wherein before, during or after the step c) further comprises:

d) reducing the pressure of the first stage effluent stream such that the propane is removed from the first stage effluent stream by evaporization, whereby m-diethylbenzene and o-diethylbenzene in liquid phase and a substantially pure gaseous propane are obtained.

20. The process of claim 19 wherein the substantially pure gaseous propane in step c) and step d) are re-compressed and recycled to the step a) or step b).

* * * * *

UNITED STATES PATENT AND TRADEMARK OFFICE
CERTIFICATE OF CORRECTION

PATENT NO. : 5,336,837
DATED : August 9, 1994
INVENTOR(S) : Chung-Sung Tan, et al.

It is certified that error appears in the above-indentified patent and that said Letters Patent is hereby corrected as shown below:

Abstract, line 15, delete "stream conaining a rich" and insert -- stream containing a rich --.

Abstract, line 18, delete "isomers procucts contained" and insert -- isomers products contained --.

Col. 3, line 48, delete "$CO_2$flow" and insert -- $CO_2$ flow --.

Figure 5:
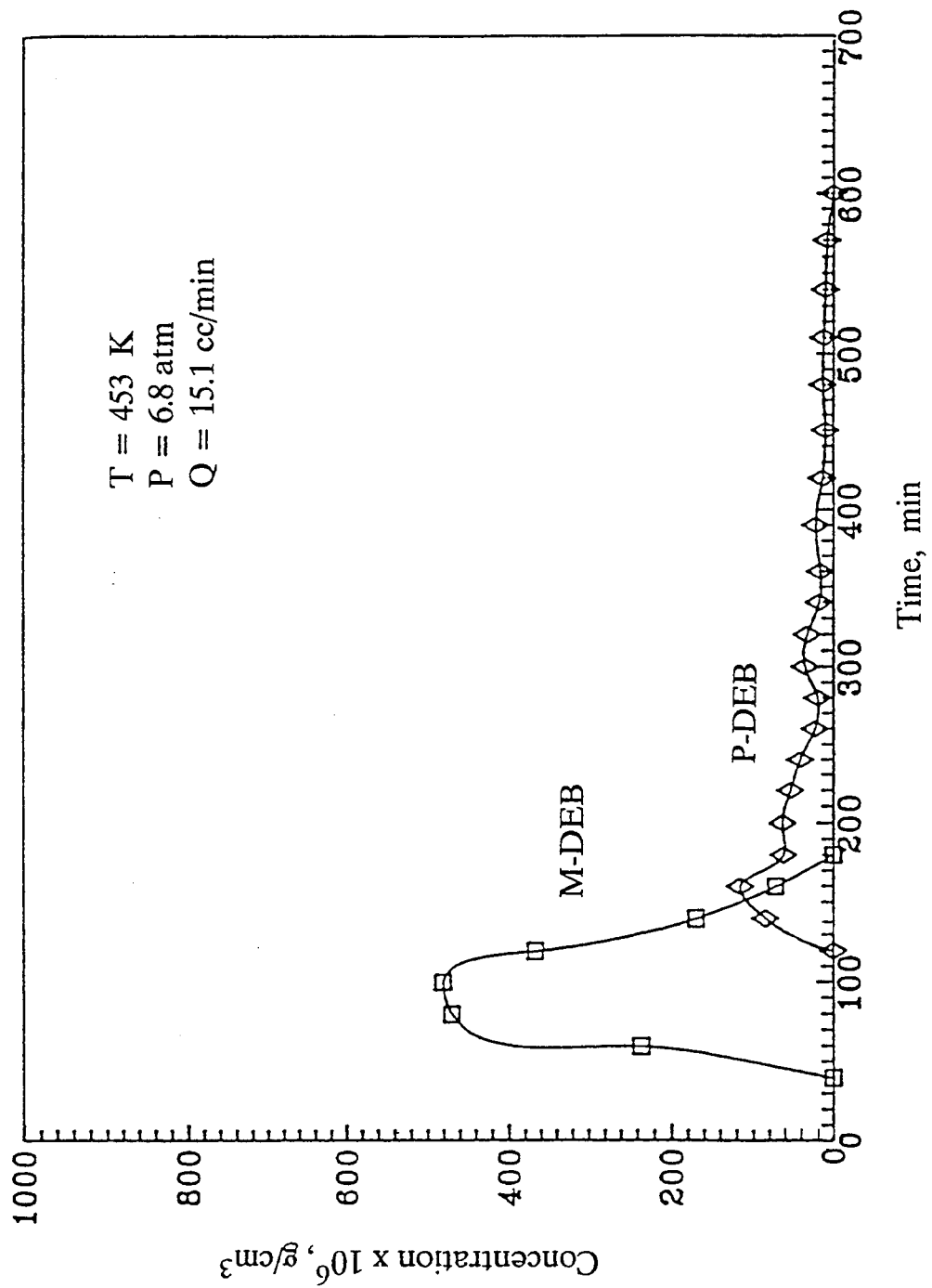
FIG. 5 plot showing the response curve of p-DEB and m-DEB under 6.8 atm, 453 K. and propane flow rate of 15.1 cc/min.
Figure 6:
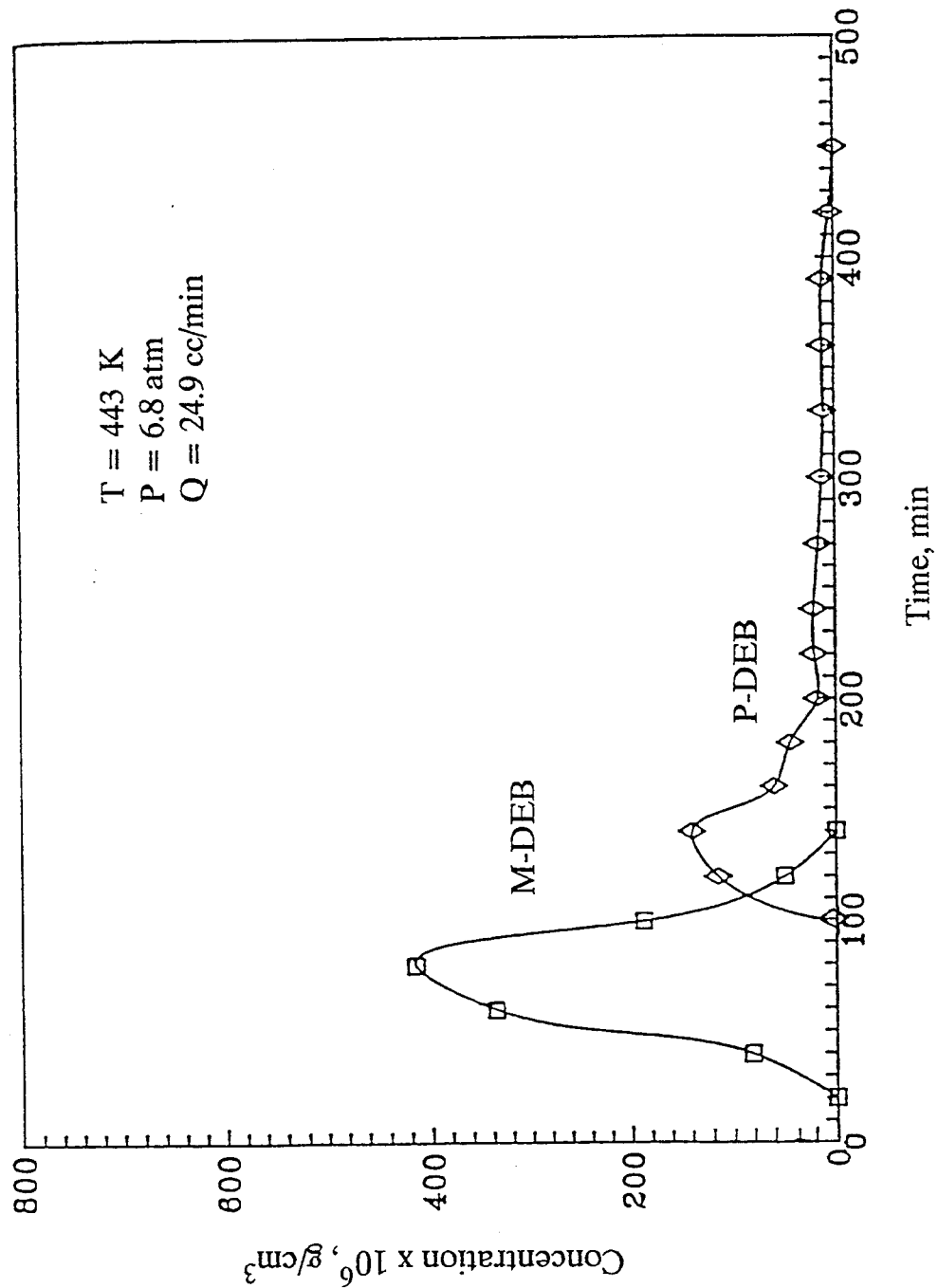
FIG. 6 is a plot showing the response curve of p-DEB and m-DEB under 6.8 atm, 443 K. and propane flow rate of 24.9 cc/min.

Col. 3, line 58, delete "FIG. 5 plot" and insert -- FIG. 5 is a plot --.

Col. 5, line 24, delete "6 Å A can" and insert -- 6 Å can --.

Col. 6, line 55, delete "pressure muse be" and insert -- pressure must be --.

Col. 10, line 41, delete "15.-40.0" and insert -- 15.0-40.0 --.

Signed and Sealed this

Twenty-third Day of May, 1995

Attest:

BRUCE LEHMAN

*Attesting Officer*   *Commissioner of Patents and Trademarks*